United States Patent [19]

Chen et al.

[11] Patent Number: 4,763,657
[45] Date of Patent: Aug. 16, 1988

[54] THERMALLY-TREATED ELECTRONIC ACUPUNCTURER

[76] Inventors: Chen-Wei Chen; Jenny Lin, both of P. O. Box 10160, Taipei, Taiwan

[21] Appl. No.: 34,531

[22] Filed: Apr. 6, 1987

[51] Int. Cl.$^4$ ............................................. A61N 1/00
[52] U.S. Cl. ................................................... 128/422
[58] Field of Search ............... 128/800, 329 A, 783, 128/24.1, 67, 421, 422; 604/20

[56] References Cited

U.S. PATENT DOCUMENTS 3,938,526  2/1976  Anderson et al. ............. 128/329 A

FOREIGN PATENT DOCUMENTS 288428  2/1967  Australia .................... 128/422

Primary Examiner—William E. Kamm
Assistant Examiner—George Manuel

[57] ABSTRACT

An electronic acupuncturer includes a casing having a handle stored with a low-frequency current generator and a head portion for fixing two acupuncturing conductors which are electrically connected with the positive and negative polarities of the current generator, and a heater also powered by the current generator adapted for producing heat auxiliarily thermally treating a patient as acupunctured by the two conductors.

4 Claims, 5 Drawing Sheets

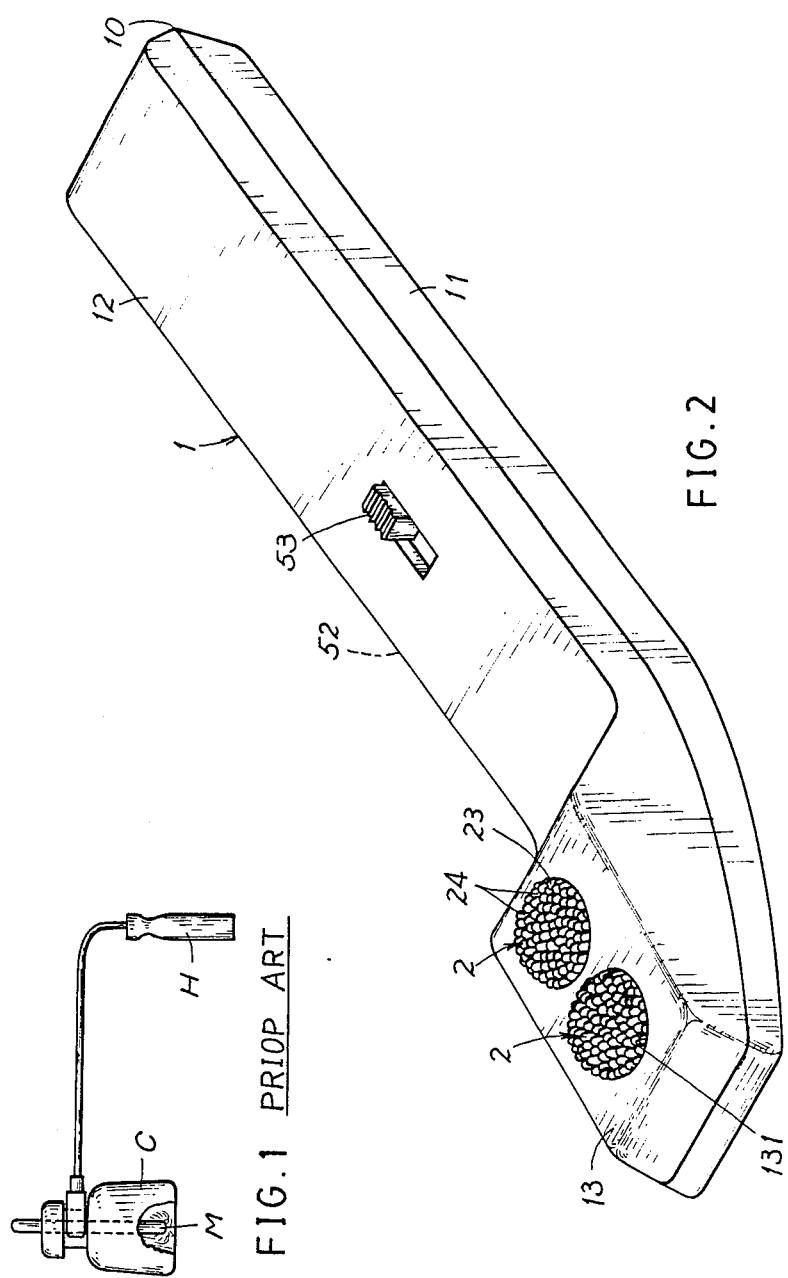

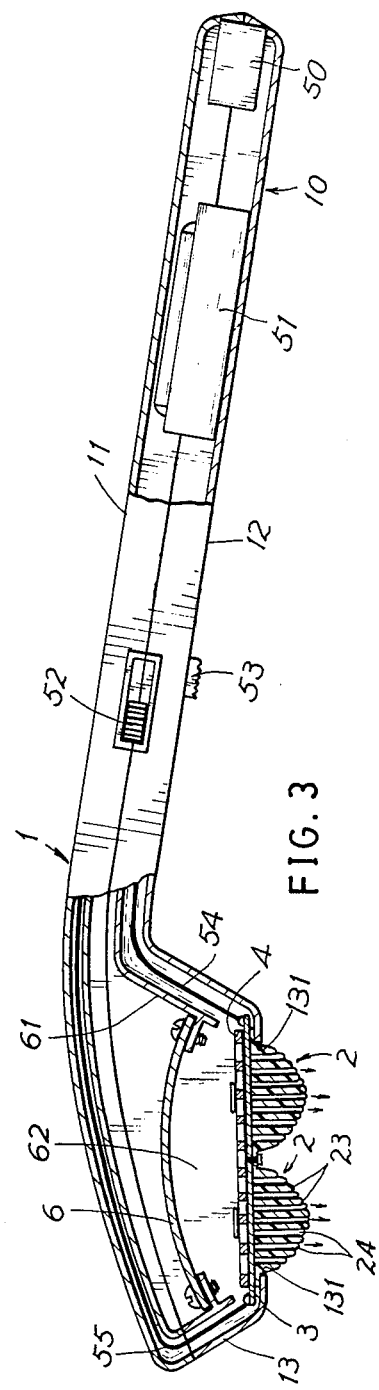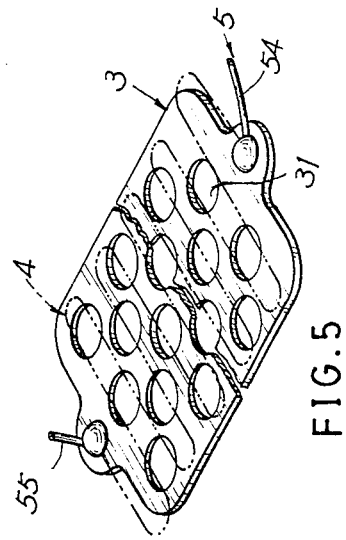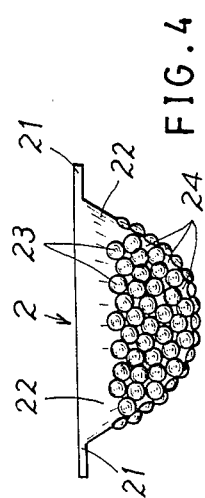
FIG. 3
FIG. 5
FIG. 4

THERMALLY-TREATED ELECTRONIC ACUPUNCTURER

BACKGROUND OF THE INVENTION

Acupuncture is an old Chinese medical treatment by inserting needles into the living tissues for remedial purposes, especially for exciting a patient's nerve endings for curing the neuralgia pain.

A thermal acupuncture is performed by using an apparatus as shown in FIG. 1 which comprises a moxa (mugwort) needle M burned within a cup C and a handle H carried by an user, adapted to acupuncture the pain spot by covering the cup C on such a pain spot. However, it is quite inconvenient to burn and operate the central moxa needle for thermal acupuncture. Whenever the moxa is used up, it may become difficult to continuously supply a new moxa (an oriental medicine) especially in an area other then oriental states such as China, Japan, etc., and may therefore interrupt the acupuncture treatment.

The present inventors have found such phenomena and invented the present thermally-treated electronic acupuncturer.

SUMMARY OF THE INVENTION

The object of the present invention is to provide a thermally-treated electronic acupuncturer including a casing, a pair of acupuncturing conductors respectively electrically connected to both positive and negative polarities of a low-frequency current device and formed on a head portion of the casing, an electric heater also powered by the low-frequency current device and fixed on a metallic substrate plate which also secures the pair of acupuncturing conductors on the substrate plate, and a heat reflector formed behind the heater adapted to reflect the heat outwardly onto the acupunctured skin area of a patient, whereby upon the powering of the low-frequency current generator and the heater, a low-frequency current and the heat is transmitted through the conductors to the patient's body to excite his or her nerve endings so as to eliminate his or her neuralgia pain or numbness.

BRIEF DESCRIPTION OF THE DRAWINGS

FIG. 1 is an illustration showing a conventional acupuncturer of old Chinese way.

FIG. 2 is a perspective view of the present invention.

FIG. 3 is a partial sectional drawing of the present invention.

FIG. 4 shows a conductor of the present invention.

FIG. 7 is a partial sectional drawing of another preferred embodiment of the present invention.

FIG. 8 is a partial perspective view of the acupuncturer as shown in FIG. 7.

DETAILED DESCRIPTION

Figure 5:
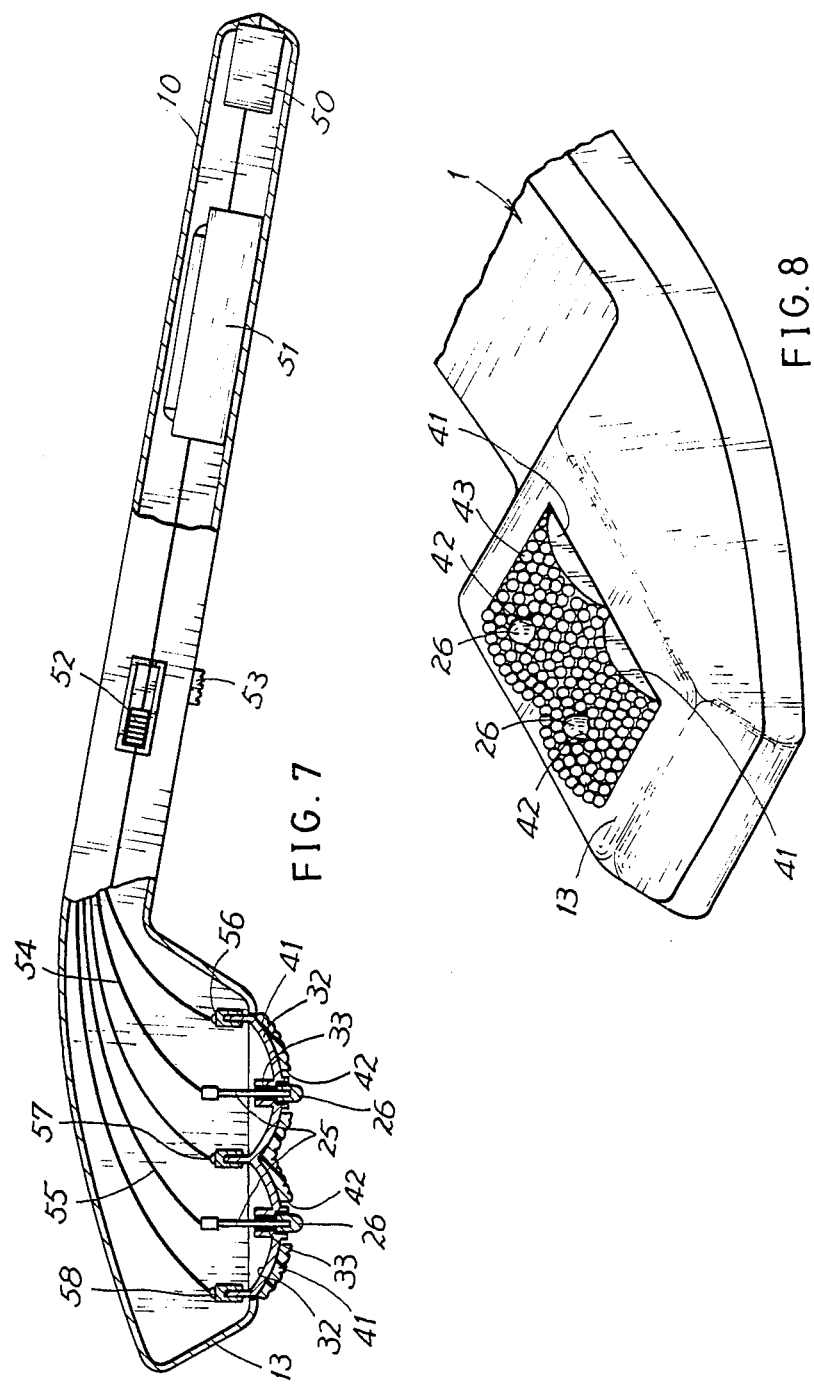
FIG. 5 is an illustration showing a metallic substrate plate and a heater of the present invention.

As shown in FIGS. 2-6, the present invention comprises a casing 1, a pair of acupuncturing conductors 2, a metallic substrate plate 3, an electric heater 4, a low-frequency current device 5, and a heat reflector 6.

The casing 1 includes: two half shells 11, 12 combined together to form the casing 1, a handle portion 10 for storing the current device 5 therein, and a head portion 13 formed with two holes 131 for fixing the pair of conductors. Several switches for controlling the current of the device 5 are provided on the handle portion 10.

Each acupuncturing conductor 2 includes a flange 21 fixed into the hole 131 on the head portion 13 of casing 2, a hemispherical portion 22 extending outwardly from the flange 21, a plurality of beads 23 formed on the surface of the hemi-spherical portion 22 adapted for acupuncture and massage purposes, and a plurality of through holes 24 formed through the conductor 2 each positioned among the neightboring beads 23 to communicate an inner cavity 62 as defined by the reflector 6 and the heater 4 for venting warm air outwardly through the holes 24 for thermal therapy purpose when applying such heat onto a patient's skin. The conductor 2 is preferably made of silicon rubber or heat-conductive rubber, capable of conducting electric current. One of the two conductors 2 is electrically connected to a positive polarity 54 and the other conductor 2 is electrically connected to a negative polarity 55 of the current device 5.

The conductors 2 are fixed on the outer side of the metallic substrate plate 3 which is drilled with plural holes 31 each being larger than the hole 24 for air flowing through such holes 31, 24. The electric heater 4 is fixed on the inner side of the substrate plate 3 and is electrically connected between two polarities 54, 55 of the current device 5. The reflector 6 is fixed inside the casing 1 by a bracket 61 as positioned behind the heater 4 and is concaved downwards to reflect the heat as radiated from the heater 4 outwardly towards a patient's skin. The heater 4 may be formed as a saw-toothed heating element secured between the two poles 54, 55 or may be formed as a heating plate secured between the two poles.

Figure 6:
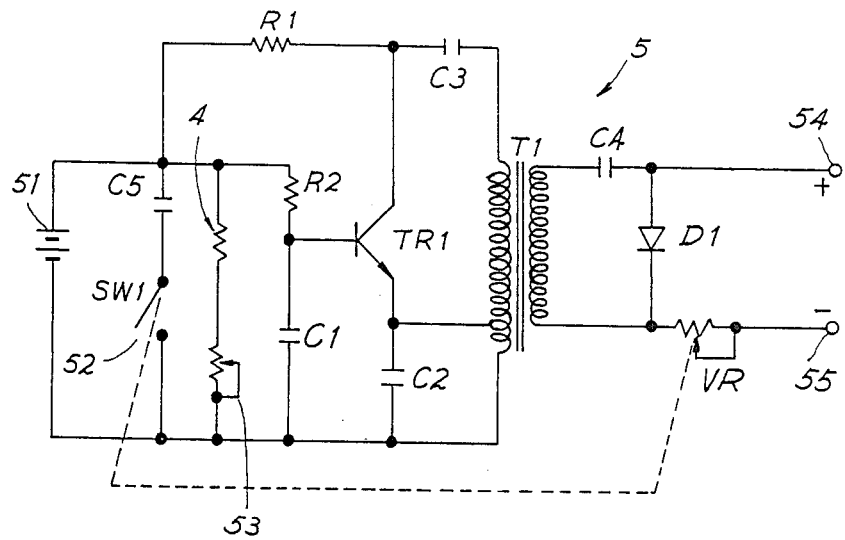
FIG. 6 is a block diagram of the electronic circuit of the low-frequency current device of the present invention.

The current device 5 as shown in FIG. 6 includes a power source generally selected from batteries 51 or rechargeable batteries electrically charged by an adapter 50 formed on the end of the handle 10, a current adjusting switch 52 including an on-off swtch SW1 and a variable resistor VR, a heat adjusting switch 53 adjusting the resistance of the heating element 4, a transistor TR1 adapted for producing oscillating low-frequency current waves, a transformer T1, several capacitors, a light-emitting diode D1 for indicating output signal, a positive polarity 54 and a negative polarity 55 for the output of low-frequency current. Such an oscillating circuit can be further modified by those skilled in the art and is not limited in this invention.

Figure 9:
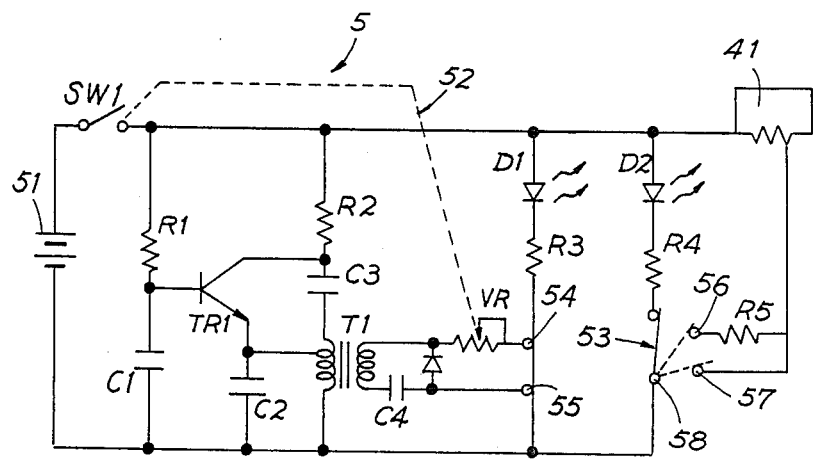
FIG. 9 is a block diagram of the electronic circuit for the acupuncturer as shown in FIG. 7.

Another preferred embodiment of the present invention is shown in FIGS. 7-9 which comprises: a casing 1 having a handle portion 10 and a head portion 13 for fixing two conductors 25, a pair of acupuncturing conductors 25 respectively electrically connected with two poles 54, 55 and each formed as an electric conducting stem 25 and jacketed with a silicon-rubber sheath 26 on its outermost end, and two curved metallic substrate plates 32 respectively coated with two curved silicon-rubber covers 41 which are adapted for partially conducting electric current and for producing heat as resistance inherently existing in the silicon-rubber covers for thermal therapy, as secured among three terminals 56, 57, 58 of a low-frequency current generator 5 as shown in FIG. 9.

The current device 5 includes the two polarities 54, 55 adapted for connecting the two conductors 25 of which the output current is adjusted by switch 52, and three terminals 56, 57, 58 connecting the two curved silicon-rubber cover 41 which are variably adjusted for the resistance of the rubber covers by a selector switch 53. As shown in FIG. 9, the terminals 56, 57 are parallelly connected to the positive polarity of the power source and the terminal 58 is connected to the negative polarity. A switch 53 is shifted to close either terminals 58, 56 or terminals 58, 57. Each rubber cover 41 is formed with a central hole 42 to protrude the conductor 25 outwardly. Each conductor 25 is insulated from the metallic plate 31 by an insulator 33 to prevent current leakage between the conductor 25 and the rubber cover (resistor) 41.

Figure 10:
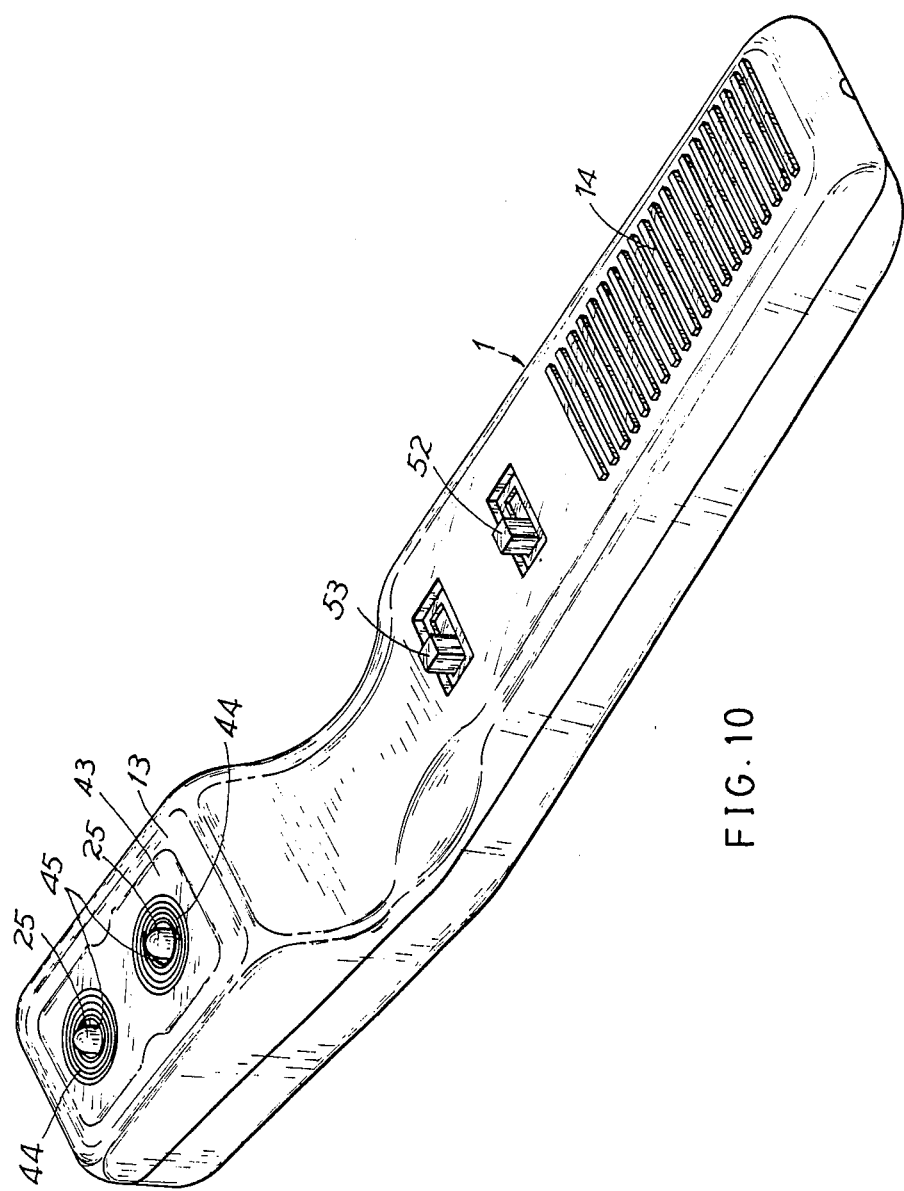
FIG. 10 shows still another preferred embodiment of the present invention.

Still another preferred embodiment of the present invention is shown in FIG. 10 which comprises a casing 1 having a head portion 13 for fixing two conductors 25 electrically conducted with a low-frequency current device 5 and a handle portion 10 formed with corrugated surface 14 to prevent slippery during portable service, and a flat siliconrubber cover 43 formed on the head portion 13 having two sets concentric circular extensions 44 formed on the cover 43 each drilled with a central hole 45 for protruding each conductor 25. The conductors 25 will acupuncture a patient's skin which is auxiliarily thermally-treated by the concentric circular extensions 44 as also electrically conducted with the current device 5 for the heat generation. The central conductors 25 also perform thermal therapy since they may produce heat through the rubber sheath 26.

The surface of the curved silicon-rubber cover 41 can be formed with beads 43 for aiding acupuncture and massage effect, besides their thermal-therapy effect or without beads 43 for merely thermal therapy purpose (FIG. 8).

Besides the silicon rubber, other materials adapted for passing current and producing heat can be used in this invention to substitute the aforementioned silicon rubber.

We claim:

1. A thermally-treated electronic acupuncture device comprising:

a casing including a handle portion and a head portion having two holes formed in said head portion;

a first acupuncturing conductor electrically connected to a positive polarity of a low-frequency current device and a second acupuncturing conductor electrically connected to a negative polarity of the current device, each said conductor including a flange fixed in each of said hole of said head portion, a hemi-spherical portion extending outwardly from each said flange, a plurality of beads formed on each said hemispherical portion, and a plurality of through-holes formed through each said conductor an electric heater and a reflector positioned behind said heater and fixed inside said head portion by a bracket, said reflector concaved downwardly for outwardly reflecting heat produced from said heater;

a metallic substrate plate having a plurality of holes formed thereineach hole formed among its neighboring beads and communicated with said inner cavity, each said conductor fixed on an outer side of said metallic substrate plate;

said electric heater to the positive and negative polarities of said current device; and said low-frequency current device including a power source having the positive and negative polarities, a transistor, a transformer and plural capacitors in functional operation and fixed in said handle portion for forming oscillating low-frequency current waves, and an adjusting switch fixed on said handle portion, having an on-off switch and a variable resistor for adjusting an output of said current device through said positive and negative polarities.

2. An acupuncture device according to claim 1, wherein said acupuncturing conductor comprises silicon rubber having electric and thermal conductivity properties.

3. An acupuncture device comprising:

a casing having a head portion and a handle portion;

a low-frequency current device having a positive polarity and a negative polarity, fixed in said handle portion; first and second acupuncturing conductors fixed on the head portion,each said conductor having an electric conducting stem, first said conducting stem electrically connected to a positive polarity of a low-frequency current device and second said conducting stem connected to a negative polarity of the current device; and two curved silicon-rubber covers respectively coated on two curved metallic substrate plates secured on said head portion and electrically connected between said positive and negative polarities, each said silicon-rubber cover being electrically and thermally conductive and having a plurality of beads formed thereon, each said conductor protruded outwardly through a central hole formed in said rubber cover and jacketed with a silicon-rubber sheath thereon.

4. An acupuncture device comprising:

a casing having a head portion and a handle portion;

a low-frequency current device having a positive polarity and a negative polarity fixed in said handle portion;

a first acupuncturing conductor electrically connected to the positive polarity of said current device and having a second acupuncturing conductor connected to the negative polarity of said current device; and a flat silicon-rubber cover, electrically and thermally conductive, formed on said head portion and electrically connected between the positive and negative polarities of said current device, said cover formed on said head portion having two holes formed therein for protruding the two conductors outwardly; and two sets of concentric circular extensions longitudinally formed on said rubber cover corresponding to said first and said second acupuncutring conductors, each set of extensions being disposed around each said conductor.

* * * * *